(12) United States Patent
Crumbaugh et al.

US006399847B1

(10) Patent No.: US 6,399,847 B1
(45) Date of Patent: *Jun. 4, 2002

(54) METHOD OF PURIFYING 1,3,5-TRIISOPROPYLBENZENE

(75) Inventors: Gretchen Crumbaugh, Wyoming; Dieter Schweiss; Jonathan Charles Walker, both of Holland, all of MI (US)

(73) Assignee: Warner-Lambert Company, Morris Plains, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/355,583

(22) PCT Filed: Dec. 5, 1997

(86) PCT No.: PCT/US97/22127

§ 371 (c)(1), (2), (4) Date: Jul. 29, 1999

(87) PCT Pub. No.: WO98/34892

PCT Pub. Date: Aug. 13, 1998

Related U.S. Application Data

(60) Provisional application No. 60/038,828, filed on Feb. 6, 1997.

(51) Int. Cl.[7] .................................................. C07C 7/17
(52) U.S. Cl. .......................... 585/856; 585/857; 585/858
(58) Field of Search ................................. 585/856, 857, 585/858

(56) References Cited

U.S. PATENT DOCUMENTS

| 2,873,300 A | | 2/1959 | Corson et al. ............... 585/585 |
| 2,761,858 A | * | 11/1972 | Hettinger et al. ........... 585/856 |
| 3,703,503 A | * | 11/1972 | Scudder ....................... 585/856 |

FOREIGN PATENT DOCUMENTS

| WO | 9834892 | 8/1998 |

OTHER PUBLICATIONS

PCT International Search Report, PCT/US97/22127.
Chemical Abstract, vol. 110, No. 6, 1989 Abstract No. 41284d, p. 135.

* cited by examiner

Primary Examiner—Walter D. Griffin
Assistant Examiner—Tam M. Nguyen
(74) Attorney, Agent, or Firm—Charles W. Ashbrook; David R. Kurlandsky

(57) ABSTRACT

The present invention relates to a method of purifying 1,3,5-triisopropylbenzene that comprises combining inpure 1,3,5-triisopropylbenzene with a sulfonating agent to form a reaction mixture, mixing the reaction mixture at a temperature in the range of about 0° C. to about 50° C., and collecting the purified 1,3,5-triisopropylbenzene.

17 Claims, No Drawings

METHOD OF PURIFYING 1,3,5-TRIISOPROPYLBENZENE

This Application claims the benefit of U.S. Provisional Application No. 60/038,828, filed on Feb. 6, 1997.

FIELD OF THE INVENTION

This invention relates to a method of purifying 1,3,5-triisopropylbenzene.

BACKGROUND OF THE INVENTION 1,3,5-Triisopropylbenzene is a known compound that can be commercially purchased. 1,3,5-Triisopropylbenzene is used in the synthesis of 2,6-bis(1-methylethyl)phenyl[[2,4,6-tris(1-methylethyl)phenyl]acetyl]sulfamate, which can be used as a lipid regulator. Because 2,6-bis(1-methylethyl)phenyl[[2,4,6-tris(1-methylethyl)phenyl]acetyl]sulfamate is a pharmaceutical intended for human use, its purity must be high. Therefore, in synthesizing 2,6-bis(1-methylethyl)phenyl[[2,4,6-tris(1-methylethyl)phenyl]acetyl]sulfamate, the purity of starting materials and intermediates in the synthesis is important. Thus, it is desirable to obtain 1,3,5-triisopropylbenzene having a high purity.

It is difficult to obtain 1,3,5-triisopropylbenzene having a purity of greater than 98% of 1,3,5-triisopropylbenzene. For example, 1,3,5-triisopropylbenzene can be purified to greater than 98% by vacuum distillation, but the distillation apparatus must contain over 120 theoretical plates, which is expensive and time consuming. Moreover, commercially available 1,3,5-triisopropylbenzene typically is not as pure as desired and must be further purified. For example, 1,3,5-triisopropylbenzene having a purity of only 97.6% can be purchased from Aldrich, Milwaukee, Wis.

The present invention provides a simple and efficient method for purifying 1,3,5-triisopropylbenzene to purities greater than 97.6% of 1,3,5-triisopropylbenzene.

SUMMARY OF THE INVENTION

The present invention provides a method of purifying 1,3,5-triisopropylbenzene that comprises combining impure 1,3,5-triisopropylbenzene with a sulfonating agent to form a reaction mixture, mixing the reaction mixture at a temperature of about 0° C. or above; and collecting the purified 1,3,5-triisopropylbenzene.

In a preferred embodiment of the method, the sulfonating agent comprises chlorosulfonic acid.

In another preferred embodiment, the sulfonating agent is about 20 mol percent of the impure 1,3,5-triisopropylbenzene.

In another preferred embodiment, the sulfonating agent is in the range of about 15 mol percent to about 30 mol percent of the impure 1,3,5-triisopropylbenzene.

In another preferred embodiment, the reaction mixture is mixed at a temperature in the range of about 0° C. to about 50° C.

In another preferred embodiment, the reaction mixture is mixed at a temperature in the range of about 20° C. to about 30° C.

In another preferred embodiment, the reaction mixture is mixed at room temperature.

In another preferred embodiment, the sulfonating agent comprises fluorosulfonic acid or sulfuric acid.

In another preferred embodiment, the reaction mixture is mixed for at least 5 minutes.

In another preferred embodiment, the reaction mixture is mixed for about 5 minutes to about 24 hours.

In another preferred embodiment, the reaction mixture is mixed for about 5 minutes to about 60 minutes.

In another preferred embodiment, the purified 1,3,5-triisopropylbenzene is collected by extracting the reaction mixture first with water, second with a base or an aqueous alcoholic solution, and last with water.

In another preferred embodiment, the purified 1,3,5-triisopropylbenzene is collected by extracting the reaction mixture with a base or an aqueous alcoholic solution.

In another preferred embodiment, the base is sodium hydroxide.

In another preferred embodiment, the sodium hydroxide has a concentration of about 5 percent to about 50 percent by weight sodium hydroxide to water.

In another preferred embodiment, the sodium hydroxide has a concentration of about 5 percent to about 20 percent by weight sodium hydroxide to water.

In another preferred embodiment, the sodium hydroxide has a concentration of about 5 percent by weight sodium hydroxide to water.

In another preferred embodiment, the base comprises sodium bicarbonate, ammonia or sodium hydroxide, or mixtures thereof.

In another preferred embodiment, the aqueous alcoholic solution is a methanol and water solution.

In a more preferred embodiment, the methanol and water solution is a 50 percent by volume methanol to water solution.

In another preferred embodiment, the base is 5 percent by weight sodium bicarbonate to water, or 30 percent by weight ammonia to water.

In a most preferred embodiment, the present invention provides a method of purifying 1,3,5-triisopropylbenzene that comprises combining impure 1,3,5-triisopropylbenzene with about 20 mole percent chlorosulfonic acid to the 1,3,5-triisopropylbenzene to form a reaction mixture, mixing the reaction mixture at a temperature in the range of about 0° C. to about 50° C. for a time in the range of about 10 minutes to about 24 hours, and collecting the purified 1,3,5-triisopropylbenzene by first extracting the reaction mixture with water, next extracting the reaction mixture with sodium hydroxide having a concentration in the range of about 5 percent to about 50 percent by weight sodium hydroxide to water, and last extracting the reaction mixture with water.

DETAILED DESCRIPTION OF THE INVENTION

The present invention provides a method of purifying 1,3,5-triisopropylbenzene that comprises combining impure 1,3,5-triisopropylbenzene with a sulfonating agent to form a reaction mixture, mixing the reaction mixture at a temperature at about 0° C. or above, and collecting the purified 1,3,5-triisopropylbenzene.

In general, impure 1,3,5-triisopropylbenzene is combined with a sulfonating agent in a suitable container such as a round-bottomed flask to form a reaction mixture, and the mixture is mixed by stirring or shaking or the like.

The term "impure 1,3,5-triisopropylbenzene" means 1,3,5-triisopropylbenzene that contains impurities that are desired to be removed. For example, 1,3,5-triisopropylbenzene that has a purity of 97.6% with respect to 1,3,5-triisopropylbenzene can be purchased from Aldrich, Milwaukee, Wis. However, it is desirable to have a purity of 98%. Preferably, the purity of the 1,3,5-triisopropylbenzene is greater than 98% and most preferably greater than 99%. The purities expressed herein are area percents obtained by vapor phase chromatography as set forth below.

The sulfonating agent can be selected from those sulfonating agents known to those skilled in the art. The sulfonating agent is preferably inexpensive and should provide for greater sulfonation of the impurities than of 1,3,5-triisopropylbenzene. In general, the major impurities seen in impure 1,3,5-triisopropylbenzene include 1,2,4-triisopropylbenzene and ethyldiisopropylbenzenes. Examples of suitable sulfonating agents include, but are not limited to, chlorosulfonic acid, fluorosulfonic acid, sulfur trioxide and sulfuric acid. Preferably, the sulfonating agent is chlorosulfonic acid.

The sulfonating agent is combined with impure 1,3,5-triisopropylbenzene in an amount that is in the range of about 15 mol to about 50 mole percent sulfonating agent to 1,3,5-triisopropylbenzene. Preferably, the sulfonating agent is used in an amount that is in the range of about 15 mol to about 30 mol percent sulfonating agent to 1,3,5-triisopropylbenzene. In a preferred embodiment, the sulfonating agent is chlorosulfonic acid, and the amount of the chlorosulfonic is 20 mol percent with respect to the 1,3,5-triisopropylbenzene.

The mixture of 1,3,5-triisopropylbenzene and the sulfonating agent are mixed by methods that are well-known to those skilled in the art at a temperature in the range of about 0° C. or above. Preferably, the temperature of the reaction mixture is in the range of about 0° C. to about 50° C. More preferably, the temperature of the reaction mixture is in the range of about 20° C. to 30° C. Most preferably, the temperature of the reaction mixture is about room temperature. In general, room temperature is about 23° C. However, room temperature can vary a few degrees. For example, room temperature can include the temperatures in the range of about 25° C. to about 20° C.

The reaction mixture is mixed at the desired temperature for at least 5 minutes. Preferably, the reaction mixture is mixed at the desired temperature in the range of about 5 minutes to about 24 hours. More preferably, the reaction mixture is mixed at the desired temperature in the range of about 5 minutes to about 60 minutes. It is noted that the reaction time necessary to obtain the desired purity of 1,3,5-triisopropylbenzene can vary depending on the temperature of the reaction mixture.

After the reaction mixture is mixed for the desired time and temperature, the purified 1,3,5-triisopropylbenzene is collected. The purified 1,3,5-triisopropylbenzene can be collected by a series of extractions or by a single extraction. For example, the purified 1,3,5-triisopropylbenzene can be collected by extracting the reaction mixture with water, then extracting the reaction mixture with a base or an aqueous alcoholic solution, and then extracting the reaction mixture with water. In general, the sulfonated impurities can be removed by extraction into an aqueous solution or by conversion of the sulfonated impurities into a salt using a base and then extracting into an aqueous solution. Typically, the volume of the extracting liquid is equal to or greater than the volume of the reaction mixture. Preferably, the volume of the extracting liquid is in the range of about one to about 10 times the volume of the reaction mixture.

Alternatively, the purified 1,3,5-triisopropylbenzene can be collected by extracting with a base using a single extraction or a series of basic extractions. In another purification method, the purified 1,3,5-triisopropylbenzene can be collected by extracting with a base using a single extraction or a series of basic extractions followed by a single or a series of extractions with water.

An aqueous alcoholic solution is a mixture that contains an alcohol and water. Examples of suitable alcohols include methanol, ethanol, propanol, isopropanol and the like.

Suitable bases are well-known to those skilled in the art. Examples of suitable bases include, but are not limited to, sodium hydroxide, ammonia, sodium bicarbonate, sodium carbonate, potassium bicarbonate, potassium carbonate, potassium hydroxide, calcium hydroxide, or mixtures thereof. Preferably, the base is sodium hydroxide.

The concentration of the base can be varied. For example, when the base is sodium hydroxide, the concentration of sodium hydroxide with respect to water can be in the range of about 5 percent to about 50 percent by weight sodium hydroxide to water. Preferably, the sodium hydroxide is about 5 percent to about 20 percent by weight sodium hydroxide to water. In a preferred embodiment of the present invention, the base is sodium hydroxide having a concentration of about 5% sodium hydroxide with respect to water.

The number of extractions and the amount of water, base, or aqueous alcoholic solution used for each extraction can be readily determined by those skilled in the art. It is also noted that more than one extraction may be performed. For example, the reaction mixture can be extracted three times with water per extraction before extraction with a base. Similarly, more than one basic extraction may be performed.

The term "purified 1,3,5-triisopropylbenzene" means 1,3,5-triisopropylbenzene that has been purified so that the level of any remaining impurities are less than the level of impurities found in the impure 1,3,5-triisopropylbenzene. Preferably, the purity of the 1,3,5-triisopropylbenzene is greater than 97% with respect to the 1,3,5-triisopropylbenzene. More preferably, the 1,3,5-triisopropylbenzene has a purity greater than 98% with respect to the 1,3,5-triisopropylbenzene, and most preferably, the purity of the 1,3,5-triisopropylbenzene is greater than 99%.

The examples presented below are intended to illustrate particular embodiments of the invention and are not intended to limit the scope of the specification, including the claims, in any way.

EXAMPLE 1

Neat impure 1,3,5-triisopropylbenzene (20 g) [no solvent was added] was placed in a round-bottom flask with 20 mol percent chlorosulfonic acid (2.28 g) with respect to 1,3,5-triisopropylbenzene to form a reaction mixture where the acid formed a second layer on the bottom of the flask. The reaction mixture was stirred rapidly at room temperature (23° C.) for 30 minutes. The reaction mixture was then quenched into 100 mL of water in a separation funnel. The bottom aqueous layer was removed, and the reaction mixture was washed with 100 mL of 5 percent sodium hydroxide to water solution. The bottom aqueous layer was removed, and the reaction mixture was washed with 100 mL of water to remove the salts formed during the base wash. The water layer was removed, and the desired purified 1,3,5-triisopropylbenzene was obtained.

EXAMPLE 2

Neat impure 1,3,5-triisopropylbenzene (200 g) [no solvent was added] was placed in a round-bottom flask and stirred. Chlorosulfonic acid (22.8 g, equal to 20 mol percent with respect to the impure 1,3,5-triisopropylbenzene was added over 15 minutes, with vigorous stirring. The reaction mixture was stirred an additional 15 minutes, then poured into 1000 mL water to quench the reaction.

The phases are allowed to separate, and the bottom aqueous layer was removed. The organic layer was then washed once with 750 mL of 5% aqueous sodium hydroxide. The phases are again separated and the water layer discarded. The organic layer was then washed a final time with 750 mL of water. The organic layer, which was purified 1,3,5-triisopropylbenzene, was retained.

It is noted that in the collection procedures that use aqueous solutions or water, the resulting purified product typically has a residual water content of less than 0.02% KF as measured by the Karl Fischer Method, which is well-known to those skilled in the art. See, for example, United States Pharmacopeia, The National Formulary, USP 23, NF 18, 1995:1840–1842, which is hereby incorporated by reference.

The following table shows the results of purification of 1,3,5-triisopropylbenzene under various conditions. The procedures above were used with the noted variations.

| Example Number | Sulfonating Agent | Amount of Sulfonating Agent | Mixing Time | % Ethyl Isomer | % 1,3,5-TIPB | % 1,2,4-TIPB |
|---|---|---|---|---|---|---|
| Impure 1,3,5-TIPB A | | | | 0.96 | 91.67 | 4.33 |
| 3 | $H_2SO_4$ | 31 mol % | 1 hr (70° C.) | 0.95 | 92.62 | 4.27 |
| 4 | $H_3SO_4$/ $FeSO_4$ | 50 mol %** | 1 hr (95° C.) | 1.00 | 92.59 | 4.28 |
| 5 | $ClSO_3H$ | 74 mol % | 25 min (60° C.) | Reaction Mixture Solidified | | |
| 6 | $ClSO_3H$ | 10 mol % | <10 min | 0.91 | 95.34 | 2.67 |
| 7 | $ClSO_3H$ | 10 mol % | 45 min | 0.91 | 95.00 | 2.82 |
| 8 | $ClSO_3H$ | 20 mol % | 45 min | 0.62 | 99.27 | 0.04 |
| 9 | $ClSO_3H$ | 15 mol % | 45 min | 0.87 | 98.01 | 0.71 |
| 10 | $ClSO_3H$ | 20 mol % | <10 min | 0.60 | 99.30 | none |
| Impure 1,3,5-TIPB B | | | | 0.68 | 97.59 | 0.93 |
| 11 | $ClSO_3H$ | 10 mol % | <5 min | 0.59 | 99.27 | 0.05 |
| 12 | $ClSO_3H$ | 10 mol % | <5 min | 0.60 | 99.23 | 0.08 |
| 13 | $ClSO_3H$ | 10 mol % | <5 min (35° C.) | 0.59 | 99.25 | none |
| 14 | $ClSO_3H$ | 10 mol % | 10 min (4° C.) | 0.60 | 98.86 | 0.26 |
| 15 | $ClSO_3H$ | 5 mol % | <5 min | 0.64 | 98.50 | 0.47 |
| 16 | $ClSO_3H$ | 10 mol % | <5 min | 0.59 | 99.10 | 0.11 |
| 17 | $ClSO_3H$ | 10 mol % | <5 min (50° C.) | 0.59 | 99.20 | 0.04 |
| 18 | $ClSO_3H$ | 20 mol % | <5 min | 0.42 | 99.46 | none |
| 19 | $ClSO_3H$ | 10 mol % | <5 min | 0.61 | 99.04 | 0.10 |
| 20 | $ClSO_3H$ | 10 mol % | <5 min | 0.60 | 99.14 | 0.05 |
| 21 | $ClSO_3H^1$ | 10 mol % | 3 hrs | 0.58 | 99.30 | none |
| 22 | $ClSO_3H^1$ | 20 mol % | 15 min | 0.40 | 99.49 | none |
| 23 | $FSO_3H$ | 15 mol % | 15 min | 0.60 | 98.25 | 0.75 |
| 24 | $FSO_3H$ | 20 mol % | <5 min | 0.60 | 97.81 | 0.81 |
| 25 | $ClSO_3H$ | 20 mol % | <5 min | 0.43 | 99.3 | none |
| 26 | $ClSO_3H$ | 20 mol % | 24 hrs | nt | nt | nt |

TIPB = Triisopropylbenzene.
nt = not tested.
Impure 1,3,5-TIPB A was used in Examples 3–10.
Impure 1,3,5-TIPB B was used in Examples 11–26.
The amount of sulfonating agent was calculated as if the impure 1,3,5-triisopropylbenzene was pure.
All reactions were run in accordance with Example 1, except Examples 21 and 22 were run in accordance with Example 2.
**Percent of sulfuric acid only; 2.05 g of iron sulfate used as a catalyst.

The base used in Examples 3–11 was 10% aqueous sodium bicarbonate. In all other Examples except 16, 19, and 20, the base was sodium hydroxide.

In Example 16, the pure 1,3,5-triisopropylbenzene was collected by first extracting with a 50:50 v/v mixture of methanol/water, next extracting with sodium hydroxide, and finally extracting with a 50:50 v/v mixture of methanol/water.

In Example 19, the pure 1,3,5-triisopropylbenzene was collected by three sequential extractions of a 50:50 v/v mixture of methanol/water.

In Example 20, the pure 1,3,5-triisopropylbenzene was collected by two sequential extractions with a 15% aqueous solution of ammonia, followed by extraction with water.

Purity Analysis

The purity of 1,3,5-triisopropylbenzene can be determined by vapor phase chromatography (VPC) as follows:

A DB 5 column [30 m×0.25 mm] (J&W, Fulsom, Calif.) is used. The injection is 1 μL. The injector temperature was 150° C. The detector temperature was 300° C., and the method of detection was flame-ionization (FID). The initial temperature of the column was 115° C. for the first 15 minutes. Then the temperature was increased 10° C. per minute until 280° C., which was maintained for 10 minutes. The peak corresponding to 1,3,5-triisopropylbenzene had a retention time (Rf) of about 17 minutes to about 18 minutes.

What is claimed is:

1. A method of purifying 1,3,5-triisopropylbenzene, the method comprising:
   a. combining impure 1,3,5-triisopropylbenzene with a sulfonating agent to form a reaction mixture;
   b. mixing the reaction mixture for about 5 minutes to about 60 minutes at a temperature in the range of about 20° C. to about 30° C.; and
   c. collecting the purified 1,3,5-triisopropylbenzene.

2. The method of claim 1 wherein the sulfonating agent comprises chlorosulfonic acid.

3. The method of claim 1 wherein the sulfonating agent is about 20 mol percent of the impure 1,3,5-triisopropylbenzene.

4. The method of claim 1 wherein the sulfonating agent is in the range of about 15 mol percent to about 30 mol percent of the impure 1,3,5-triisopropylbenzene.

5. The method of claim 1 wherein the reaction mixture is mixed at room temperature.

6. The method of claim 1 wherein the sulfonating agent comprises fluorosulfonic acid or sulfuric acid.

7. The method of claim 1 wherein purified 1,3,5-triisopropylbenzene is collected by extracting the reaction mixture first with water, second with a base or an aqueous alcoholic solution, and last with water.

8. The method of claim 1 wherein the purified 1,3,5-triisopropylbenzene is collected by extracting the reaction mixture with a base or an aqueous alcoholic solution.

9. The method of claim 7 wherein the base is sodium hydroxide.

10. The method of claim 9 wherein the sodium hydroxide has a concentration of about five to about fifty percent by weight sodium hydroxide to water.

11. The method of claim 9 wherein the sodium hydroxide has a concentration of about 5 percent to about 20 percent by weight sodium hydroxide to water.

12. The method of claim 9 wherein the sodium hydroxide has a concentration of about 5 percent by weight sodium hydroxide to water.

13. The method of claim 7 wherein the base comprises sodium bicarbonate, ammonia or sodium hydroxide, or mixtures thereof.

14. The method of claim 7 wherein the aqueous alcoholic solution is a methanol and water solution.

15. The method of claim 8 wherein the aqueous alcoholic solution is a methanol and water solution.

16. The method of claim 13 wherein the base is 5 percent by weight sodium bicarbonate to water or 30 percent by weight ammonia to water.

17. A method of purifying 1,3,5-triisopropylbenzene, the method comprising:
   a. combining impure 1,3,5-triisopropylbenzene with about 20 mol percent chlorosulfonic acid to the 1,3,5-triisopropylbenzene to form a reaction mixture;
   b. mixing the reaction mixture at a temperature in the range of about 20° C. to about 30° C. for a time in the range of about 5 minutes to about 60 minutes; and
   c. collecting the purified 1,3,5-triisopropylbenzene by first extracting the reaction mixture with water, next extracting the reaction mixture with sodium hydroxide having a concentration in the range of about 5 percent to about 50 percent by weight sodium hydroxide to water, and last extracting the reaction mixture with water.

* * * * *